(12) United States Patent
Terashi et al.

(10) Patent No.: US 10,492,806 B2
(45) Date of Patent: Dec. 3, 2019

(54) MEDICAL GUIDE WIRE

(71) Applicant: FMD Co., Ltd., Toda-shi, Saitama (JP)

(72) Inventors: Tsuyoshi Terashi, Toda (JP); Seiji Shimura, Toda (JP)

(73) Assignee: FMD Co., Ltd., Toda-shi, Saitama (JP)

( * ) Notice: Subject to any disclaimer, the term of this patent is extended or adjusted under 35 U.S.C. 154(b) by 113 days.

(21) Appl. No.: 15/717,950

(22) Filed: Sep. 28, 2017

(65) Prior Publication Data

US 2018/0092651 A1    Apr. 5, 2018

(30) Foreign Application Priority Data

Sep. 30, 2016  (JP) ................................. 2016-205555

(51) Int. Cl.
*A61B 5/00* (2006.01)
*A61B 17/22* (2006.01)
(Continued)

(52) U.S. Cl.
CPC ............ *A61B 17/22* (2013.01); *A61L 31/022* (2013.01); *A61L 31/10* (2013.01); *A61M 25/09* (2013.01);
(Continued)

(58) Field of Classification Search
CPC .......... A61B 17/22; A61B 2017/00477; A61B 2017/00862; A61B 2017/00867;
(Continued)

(56) References Cited

U.S. PATENT DOCUMENTS

| 5,341,818 A | 8/1994 | Abrams et al. |
| 2002/0121316 A1 | 9/2002 | Abrams et al. |

(Continued)

FOREIGN PATENT DOCUMENTS

| EP | 2551363 A | 1/2013 |
| JP | 2004-135823 A | 5/2004 |

(Continued)

OTHER PUBLICATIONS

Extended European Search Report dated Feb. 26, 2018.
(Continued)

*Primary Examiner* — Navin Natnithithadha
*Assistant Examiner* — Andrey Shostak
(74) *Attorney, Agent, or Firm* — Yokoi & Co., U.S.A.; Toshiyuki Yokoi

(57) ABSTRACT

In a medical guide wire having a connecting structure formed by three members: a tubular connector; a first core; and a second core, when a torsional rigidity of one member is lower than the torsional rigidity of the materials of both end portions, for example, the twist is unevenly generated between the members and the rotation transmission performance to the distal end side is significantly reduced. In such a case, there is a technical problem for improving the rotation transmission performance to the distal end side. In the connecting structure formed by three members, as a result of focusing on the torsional rigidity of the three members and considering the torsional rigidity ratios between the members, the technical problem for improving the rotation transmission performance to the distal end side can be solved when the torsional rigidity ratios satisfy a predetermined relation.

3 Claims, 5 Drawing Sheets

(51) Int. Cl.
*A61L 31/02* (2006.01)
*A61L 31/10* (2006.01)
*A61M 25/09* (2006.01)
*A61B 17/00* (2006.01)

(52) U.S. Cl.
CPC ............ *A61B 2017/00477* (2013.01); *A61B 2017/00862* (2013.01); *A61B 2017/00867* (2013.01); *A61B 2017/00942* (2013.01); *A61B 2017/22038* (2013.01); *A61M 2025/0915* (2013.01); *A61M 2025/09075* (2013.01); *A61M 2025/09108* (2013.01); *A61M 2025/09133* (2013.01); *A61M 2025/09166* (2013.01)

(58) Field of Classification Search
CPC .......... A61B 2017/00942; A61B 2017/22038; A61L 31/10; A61L 31/022; A61M 25/09; A61M 2025/09075; A61M 2025/09108; A61M 2025/09133; A61M 2025/0915; A61M 2025/09166
See application file for complete search history.

(56) References Cited

U.S. PATENT DOCUMENTS

| | | |
|---|---|---|
| 2003/0069520 A1 | 4/2003 | Skujins et al. |
| 2004/0106878 A1 | 6/2004 | Skujins et al. |
| 2006/0122537 A1* | 6/2006 | Reynolds .............. A61L 31/022 600/585 |
| 2008/0064989 A1 | 3/2008 | Chen et al. |
| 2008/0154152 A1 | 6/2008 | Satou et al. |
| 2008/0171952 A1 | 7/2008 | Mishima |
| 2009/0036834 A1* | 2/2009 | Voeller .............. A61M 25/0013 604/164.13 |
| 2009/0243225 A1* | 10/2009 | Matsushima ............ F16J 9/062 277/467 |
| 2013/0204163 A1* | 8/2013 | Simpson .............. C22C 19/055 600/585 |
| 2015/0157830 A1* | 6/2015 | Miyata .................. A61M 25/09 604/528 |

FOREIGN PATENT DOCUMENTS

| | | | |
|---|---|---|---|
| JP | 2005-528126 A | 9/2005 | |
| JP | 2006-508739 A | 3/2006 | |
| JP | 2008-161219 A | 7/2008 | |
| JP | 2010-503484 A | 2/2010 | |
| JP | 2010-227136 A | 10/2010 | |
| JP | 2010227136 A * | 10/2010 | ............ A61M 25/01 |
| JP | 2011-206174 A | 10/2011 | |
| JP | 2013-116252 A | 6/2013 | |
| WO | 99/19017 A | 4/1999 | |
| WO | 03/030982 A | 4/2003 | |
| WO | 2006/002199 A | 1/2006 | |
| WO | 2013/084599 A | 6/2013 | |

OTHER PUBLICATIONS

Japanese notice of the reason for refusal dated Oct. 24, 2017.
Japanese notice of the reason for refusal dated Mar. 27, 2018.
Japanese notice of the reason for refusal dated May 16, 2017.

* cited by examiner

MEDICAL GUIDE WIRE

CROSS-REFERENCES TO RELATED APPLICATIONS

This patent specification is based on Japanese patent application, No. 2016-205555 filed on Sep. 30, 2016 in the Japan Patent Office, the entire contents of which are incorporated by reference herein.

BACKGROUND OF THE INVENTION

1. Field of the Invention

The present invention relates to a medical guide wire used for treatment of an occluded lesion of a blood vessel or the like.

2. Description of Related Art

Conventionally, in the treatment of the vascular lesion such as stenosis and the completely occluded lesion of the blood vessel, a medical guide wire (hereafter, referred to as a guide wire) formed by directly welding the proximal end and the distal end of two cores or a guide wire formed by inserting both ends of the cores into a tubular member to connect the cores is used for making a distal end portion having flexibility reach the lesion. Thus, the stenosis and the completely occluded lesion of the blood vessel are treated by expanding the diameter of the blood vessel.

In the above described case, the guide wire is penetrated through the vascular lesion. Thus, a high rotation transmission performance from a proximal end side (rear side) to a distal end side, a perforation performance and a fatigue resistance against continuous use are required.

In particular, the above described performances are required for the guide wire formed by connecting different kinds of metal wires between the distal end side and the proximal end side.

Patent document 1 discloses a guide wire formed by connecting a distal end side core arranged at the distal end area and a rear end side core arranged at the proximal end area with each other using a tubular connector.

Patent document 2 discloses a guide wire formed by connecting metal wires made by different kinds of materials with each other by a connecting member.

[Patent document 1] Japanese Unexamined Patent Application Publication (Translation of PCT Application) No. 2010-503484

[Patent document 2] Japanese Unexamined Patent Application Publication No. 2004-135823

BRIEF SUMMARY OF THE INVENTION

In the guide wire described in Patent document 1, the proximal end of a linear elastic metal or the like which is linearized and arranged at the distal end area is connected with the distal end of a stainless steel wire or the like which is linearized and arranged at the proximal end area by welding, brazing or the like using the tubular connector. Thus, Patent document 1 is a technology for improving operability of an operator.

In the guide wire described in Patent document 2, an insertion portion having superior deformability and an introduction portion having superior torque transmission performance are wound by a coil-shaped connection member and then reduced in diameter. Thus, Patent document 2 is a technology for improving connection strength.

Both Patent documents 1 and 2 have a connection structure of connecting different kinds of metal wires using a tubular member in the core of the guide wire. However, different from the present invention, both documents do not disclose the technology of remarkably improving the rotation transmission performance from the proximal end side to the distal end side by focusing on torsional rigidity ratios between a tubular connector (i.e., tubular member) and each of the different kinds of metal wires and specifying the torsional rigidity ratios to satisfy a predetermined relation at the connection portion. The above described technology is an important technical problem to let the guide wire be inserted into the vascular lesion.

The present invention provides a guide wire capable of remarkably improving passability at the vascular lesion.

In the guide wire of the present invention, a proximal end of a first core and a distal end of a second core are connected and fixed to each other by a tubular connector. The first core has a pseudoelastic property and includes a small diameter proximal connection portion and a first core-large diameter proximal portion in order from the proximal end to the distal end.

The second core has a strain-induced martensitic transformation phase and includes a second core-large diameter portion and a small diameter distal connection portion in order from the proximal end to the distal end.

The small diameter proximal connection portion is inserted into the tubular connector from one side of the tubular connector and the small diameter distal connection portion is inserted into the tubular connector from the other side of the tubular connector.

One end of the tubular connector is in contact with a first step between the first core-large diameter proximal portion and the small diameter proximal connection portion, the first core-large diameter proximal portion having a larger outer diameter than the small diameter proximal connection portion.

The other end of the tubular connector is in contact with a second step between the second core-large diameter portion and the small diameter distal connection portion, the second core-large diameter portion having a larger outer diameter than the small diameter distal connection portion.

The tubular connector is connected and fixed to the first core-large diameter proximal portion at least at a first contact position between the one end of the tubular connector and the first core-large diameter proximal portion. The tubular connector is connected and fixed to the second core-large diameter portion at least at a second contact portion between the other end of the tubular connector and the second core-large diameter portion.

When a torsional rigidity of the first core-large diameter proximal portion is defined as K1, a torsional rigidity of the second core-large diameter portion is defined as K2 and a torsional rigidity of the tubular connector is defined as J1, a torsional rigidity ratio (J1/K1) of the torsional rigidity J1 of the tubular connector with respect to the torsional rigidity K1 of the first core-large diameter proximal portion and a torsional rigidity ratio (K2/K1) of the torsional rigidity K2 of the second core-large diameter portion with respect to the torsional rigidity K1 of the first core-large diameter proximal portion satisfy a predetermined relational expression.

The first core-large diameter proximal portion and the tubular connector have a pseudoelastic property, and are a Ni—Ti alloy having the transverse elastic modulus of between 17650 Mpa and 21575 Mpa when an austenite phase is exhibited. The second core-large diameter portion is an austenitic stainless steel wire having the transverse elastic modulus of 68500 Mpa or more. The torsional rigidity ratio (J1/K1) of the torsional rigidity J1 of the tubular connector with respect to the torsional rigidity K1 of the first core-large diameter proximal portion and the torsional rigidity ratio (K2/K1) of the torsional rigidity K2 of the second core-large diameter portion with respect to the torsional rigidity K1 of the first core-large diameter proximal portion satisfy a predetermined relational expression.

A proximal end of a first core and a distal end of a second core are connected and fixed to each other by a tubular connector.

The first core has a pseudoelastic property and includes a small diameter proximal connection portion and a first core-large diameter proximal portion in order from the proximal end to the distal end.

The second core has a strain-induced martensitic transformation phase and includes a second core-large diameter portion and a small diameter distal connection portion in order from the proximal end to the distal end.

The tubular connector has a constant outer diameter over an entire length. The small diameter proximal connection portion having a first small diameter proximal portion is inserted into the tubular connector from one side of the tubular connector, the first small diameter proximal portion having a first tapered portion. The small diameter distal connection portion having a first small diameter distal portion is inserted into the tubular connector from the other side of the tubular connector, the first small diameter distal portion having a second tapered portion.

A first inner end portion of one side of the tubular connector is in contact with the first tapered portion of the first small diameter proximal portion.

A second inner end portion of the other side of the tubular connector is in contact with the second tapered portion of the first small diameter distal portion.

The tubular connector is connected and fixed to the small diameter proximal connection portion at least at a first contact position between the first inner end of the one side of the tubular connector and the small diameter proximal connection portion. The tubular connector is connected and fixed to the small diameter distal connection portion at least at a second contact portion between the second inner end portion of the other side of tubular connector and the small diameter distal connection portion.

When a torsional rigidity of the small diameter proximal connection portion is defined as k11, a torsional rigidity of the small diameter distal connection portion is defined as k22 and a torsional rigidity of the tubular connector is defined as J1, a torsional rigidity ratio (J1/k11) of the torsional rigidity J1 of the tubular connector with respect to the torsional rigidity k11 of the small diameter proximal connection portion and a torsional rigidity ratio (k22/k11) of the torsional rigidity k22 of the small diameter distal connection portion with respect to the torsional rigidity k11 of the small diameter proximal connection portion satisfy a predetermined relational expression.

The tubular connector has a pseudoelastic property. The small diameter proximal connection portion and the tubular connector are a Ni—Ti alloy having the transverse elastic modulus of between 17650 Mpa and 21575 Mpa when an austenite phase is exhibited. The small diameter distal connection portion is an austenitic stainless steel wire having the transverse elastic modulus of 68500 Mpa or more. The torsional rigidity ratio (J1/k11) of the torsional rigidity J1 of the tubular connector with respect to the torsional rigidity k11 of the small diameter proximal connection portion and the torsional rigidity ratio (k22/k11) of the torsional rigidity k22 of the small diameter distal connection portion with respect to the torsional rigidity k11 of the small diameter proximal connection portion satisfy a predetermined relational expression.

A hydrophilic coating is formed at least on the outer periphery of the tubular connector and the outer periphery of the first core-large diameter proximal portion.

The guide wire of the present invention is characterized in that the second core-large diameter portion located at the proximal end side and having the strain-induced martensitic transformation phase is connected and fixed to the first core-large diameter proximal portion located at the distal end side and having the pseudoelastic property by the tubular connector, and the torsional rigidity ratio (J1/K1) of the torsional rigidity J1 of the tubular connector located at the proximal end side and the torsional rigidity ratio (K2/K1) of the torsional rigidity K2 of the second core-large diameter portion located at the proximal end side with respect to the torsional rigidity K1 of the first core-large diameter proximal portion located at the distal end side satisfy a predetermined relational expression where the torsional rigidity ratio is gradually increased from the distal end side to the proximal end side.

The above described configuration is adopted for improving the rotation transmission performance from the proximal end side to the distal end side.

Consequently, reachability to the vascular lesion and passing performance in the vascular lesion can be improved although the guide wire is formed by connecting different kinds of metal wires by the tubular connector.

The first core-large diameter proximal portion and the tubular connector have a pseudoelastic property, the first core-large diameter proximal portion and the tubular connector are a Ni—Ti alloy having a predetermined transverse elastic modulus when an austenite phase is exhibited, the second core-large diameter portion is an austenitic stainless steel wire having a predetermined transverse elastic modulus or more, and the torsional rigidity ratio (J1/K1) of the torsional rigidity J1 of the tubular connector located at the proximal end side and the torsional rigidity ratio (K2/K1) of the torsional rigidity K2 of the second core-large diameter portion located at the proximal end side with respect to the torsional rigidity K1 of the first core-large diameter proximal portion located at the distal end side satisfy a predetermined relational expression where the torsional rigidity ratio is gradually increased from the distal end side to the proximal end side within the range exceeding 1 and equal to or less than 5.85.

The above described configuration is adopted for further improving the rotation transmission performance from the proximal end side to the distal end side. Consequently, reachability to the vascular lesion and passing performance in the vascular lesion can be further improved although the guide wire is formed by connecting different kinds of metal wires by the tubular connector.

The small diameter proximal connection portion located at the distal end side and having a pseudoelastic property is connected and fixed to the small diameter distal connection portion located at the proximal end side and having a strain-induced martensitic transformation phase by the tubular connector, and the torsional rigidity ratio (J1/k11) of the torsional rigidity J1 of the tubular connector with respect to the torsional rigidity k11 of the small diameter proximal connection portion and the torsional rigidity ratio (k22/k11) of the torsional rigidity k22 of the small diameter distal connection portion with respect to the torsional rigidity k11 of the small diameter proximal connection portion satisfy a predetermined relational expression where the torsional rigidity ratio is gradually increased from the distal end side.

The above described configuration is adopted for preventing the twist from being partly and unevenly generated at the connection portion formed by connecting different kinds of metal wires when the proximal end side is rotated. Consequently, the rotation transmission performance to the distal end side and the perforation performance can be improved. Furthermore, operability can be improved.

The small diameter proximal connection portion and the tubular connector have a pseudoelastic property, the small diameter proximal connection portion and the tubular connector are a Ni—Ti alloy having a predetermined transverse elastic modulus when an austenite phase is exhibited, the small diameter distal connection portion is an austenitic stainless steel wire having a predetermined transverse elastic modulus or more, and the torsional rigidity ratio (J1/k11) of the torsional rigidity J1 of the tubular connector located at the proximal end side and the torsional rigidity ratio (k22/k11) of the small diameter proximal connection portion k22 located at the proximal end side with respect to the torsional rigidity k11 of the small diameter proximal connection portion located at the distal end side satisfy a predetermined relational expression where the torsional rigidity ratio is gradually increased from the distal end side to the proximal end side within the range exceeding 1 and equal to or less than 5.00.

The above described configuration is adopted for further preventing the twist from being partly and unevenly generated at the connection portion formed by connecting different kinds of metal wires when the proximal end side is rotated. Consequently, the rotation transmission performance to the distal end side and the perforation performance are further improved. Furthermore, operability can be further improved.

A hydrophilic coating is formed at least on the outer periphery of the tubular connector and the outer periphery of the first core-large diameter proximal portion.

Consequently, even though the guide wire has the connection portion formed by connecting different kinds of metal wires having different torsional rigidity, slidability can be improved with respect to a catheter or the like which moves in the forward/backward direction on the outside of the guide wire.

Furthermore, when the guide wire is caught by the blood vessel wall or the like during hand operation because of contraction of the blood vessel or other reasons, the guide wire can be easily released from the caught region if the hydrophilic coating is formed on the connection portion where the slidability particularly deteriorates.

DETAILED DESCRIPTION OF THE INVENTION

Hereafter, embodiments of a guide wire of the present invention will be explained.

Figure 1:
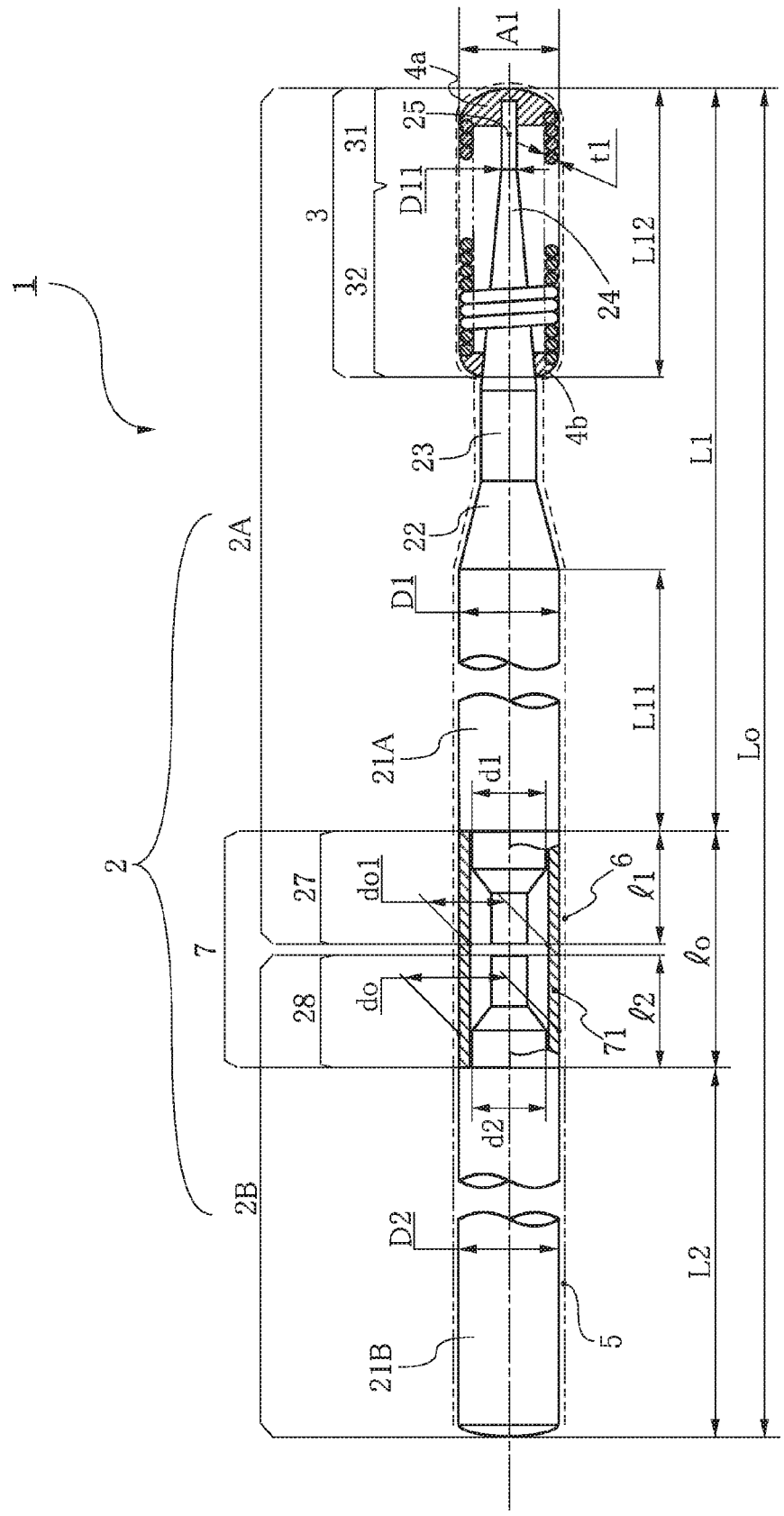
FIG. 1 is a partially cutaway side view showing whole a guide wire concerning the first embodiment of the present invention.
Figure 2:
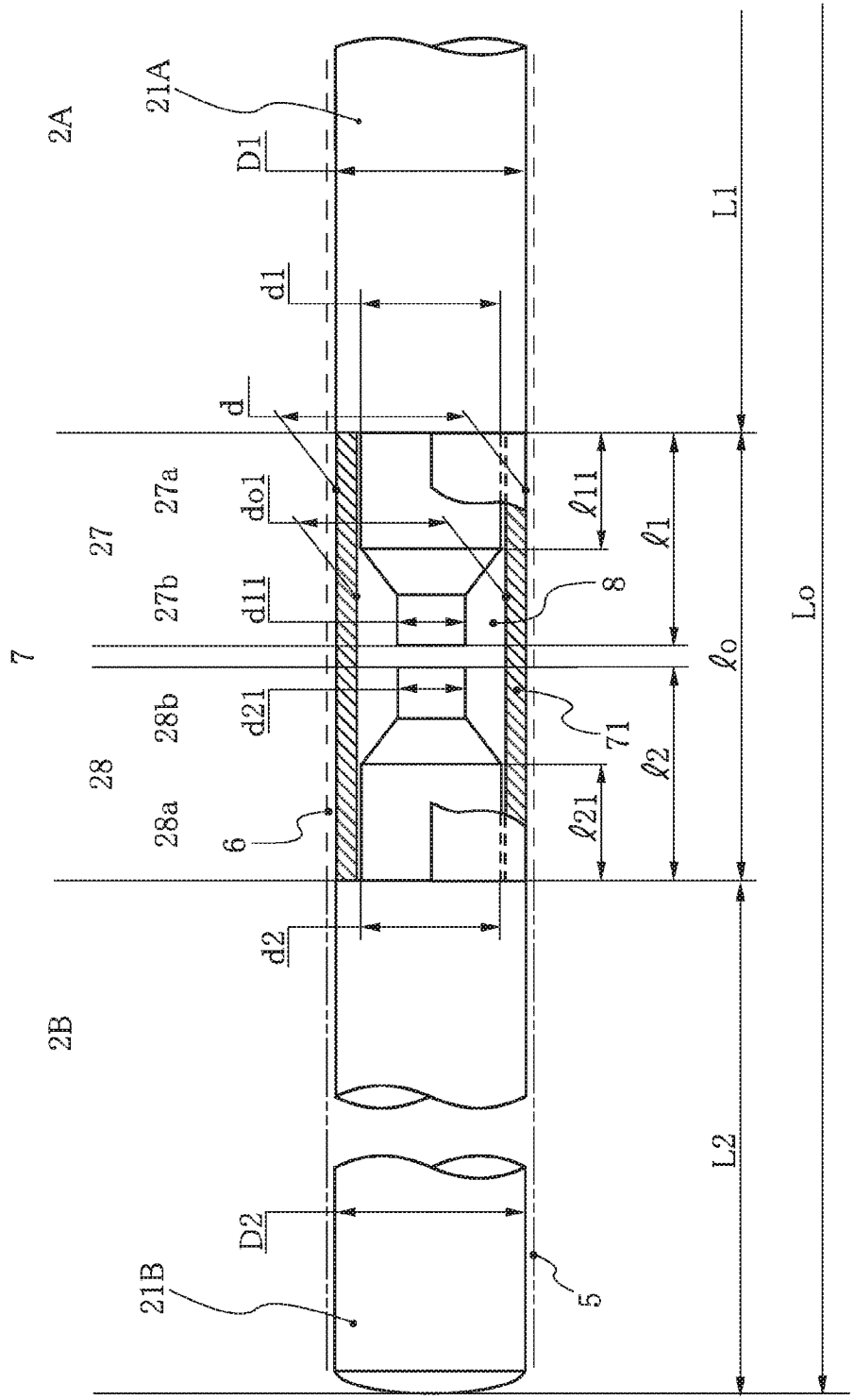
FIG. 2 is an enlarged partially cutaway side view of a main part of a connection portion concerning the first embodiment of the present invention.

FIG. 1 shows a guide wire 1 concerning the first embodiment of the present invention. FIG. 1 shows an overall view, and FIG. 2 shows a main part of a connection portion 7.

The guide wire 1 has a core 2, a tubular connector 71, a coil body 3, a fluorocarbon polymer coating 5 and a lubricative coating 6.

The core 2 has a first core 2A arranged at the distal end side and a second core 2B arranged at the proximal end side. The tubular connector 71 connects and fixes the proximal end portion of the first core 2A and the distal end side of the second core 2B.

The first core 2A has a small diameter proximal connection portion 27 located at the proximal end portion and has a first core-large diameter proximal portion 21A. In addition, the first core 2A has a portion gradually tapered in diameter from the first core-large diameter proximal portion 21A to the distal end side. The first core 2A has a first tapered portion 22, a first constant diameter portion 23, a second tapered portion 24 and a second constant diameter portion 25.

The second core 2B has a small diameter distal connection portion 28 located at the distal end portion and has a second core-large diameter portion 21B.

The small diameter proximal connection portion 27 of the first core 2A is inserted into the tubular connector 71 from one side of the tubular connector 71, and the small diameter distal connection portion 28 of the second core 2B is inserted into the tubular connector 71 from the other side of the tubular connector 71. The one side of the tubular connector 71 is connected and fixed to the first core-large diameter proximal portion 21A of the first core 2A, and the other side of the tubular connector 71 is connected and fixed to the second core-large diameter portion 21B of the second core 2B.

The coil body 3 has a radioopaque coil body 31 at the distal end side, and a radiolucent coil body 32 at the proximal end side. The second tapered portion 24 and the second constant diameter portion 25 are inserted into the coil body 3. By using a joining member, the distal end of the coil body 3 and the distal end of the second constant diameter portion 25 are joined to form a distal joining portion 4a, and the proximal end of the coil body 3 and the proximal end of the second tapered portion 24 are joined to form a proximal joining portion 4b.

It is enough if the fluorocarbon polymer coating 5 is formed at least on the outer periphery of the second core-large diameter portion 21B of the second core 2B. However, the fluorocarbon polymer coating 5 can be also formed on the outer peripheries of the first core-large diameter proximal portion 21A, the first tapered portion 22 and the first constant diameter portion 23 of the first core 2A.

The lubricative coating 6 is formed at least on the outer peripheries of the coil body 3, the distal joining portion 4a and the proximal joining portion 4b. It is preferred that the hydrophilic coating is formed on the outer periphery of the tubular connector 71 and the outer periphery of the first core-large diameter proximal portion 21A of the first core 2A.

In the guide wire 1, a length L1 of the first core 2A arranged at the distal end side of the core 2 is 600 mm, a length L2 of the second core 2B arranged at the proximal end side is 1765 mm, a length lo of the tubular connector 71 is 35 mm, and a total length Lo is 2400 mm.

In the first core-large diameter proximal portion 21A, a length L11 is 100 mm and an outer diameter D1 is 0.312 mm.

The small diameter proximal connection portion 27 located at the proximal end portion of the first core 2A has a first small diameter proximal portion 27a and a second small diameter proximal portion 27b. In the first small diameter proximal portion 27a, a length l1 is 17 mm, a length l11 is 11 mm, and an outer diameter d1 is 0.220 mm. In the second small diameter proximal portion 27b, a length is 6 mm, an outer diameter is gradually reduced from 0.220 mm to 0.100 mm, and an outer diameter d11 is a constant diameter of 0.100 mm.

The proximal end of the second core-large diameter portion 21B of the second core 2B is formed in an arc shape having a longitudinal length of 2 mm or less. In the second core-large diameter portion 21B, a length L2 is 1765 mm and an outer diameter D2 is 0.340 mm.

The small diameter distal connection portion 28 located at the distal end portion of the second core 2B has a first small diameter distal portion 28a and a second small diameter distal portion 28b. In the first small diameter distal portion 28a, a length l2 is 17 mm, a length l21 is 11 mm and an outer diameter d2 is 0.220 mm. In the second small diameter distal portion 28b, a length is 6 mm, an outer diameter is gradually reduced from 0.220 mm to 0.100 mm and an outer diameter d21 is a constant diameter of 0.100 mm.

In the tubular connector 71, a length lo is 35 mm, an outer diameter d0o is 0.356 mm and an inner diameter do1 is 0.256 mm. The small diameter proximal connection portion 27 having the length l1 of 17 mm is inserted into the tubular connector 71 from one side of the tubular connector 71, and the small diameter distal connection portion 28 having the length l2 of 17 mm is inserted into the tubular connector 71 from the other side of the tubular connector 71.

In the first core 2A, an outer diameter D1 of the first core-large diameter proximal portion 21A is 0.312 mm and an outer diameter D11 of the second constant diameter portion 25 located at the distal end side is a constant diameter of 0.08 mm. In addition, the first core 2A has a portion gradually tapered in diameter to the distal end side. Although the second constant diameter portion 25 is formed in a circular shape in the cross section having a longitudinal length of 10 mm, the cross sectional shape can be formed in a rectangular shape by pressing.

For the first core 2A, Ni—Ti alloy or Ni—Ti based alloy having a pseudoelastic property is used, for example. Here, the pseudoelastic property is an apparent elastic property which is not due to the change of interatomic spacing but generated in the mechanism of twinning deformation or the like. The pseudoelastic property includes shape-memory effect and superelasticity (transformation pseudoelasticity or twin pseudoelasticity).

Specifically, the pseudoelastic property is, for example, superelastic metal (Ni—Ti alloy) shown in Japanese Examined Patent Application Publication No. H2-24548 or the like, work hardening Ni—Ti based alloy shown in Japanese Examined Patent Application Publication No. H6-83726 or the like, wide strain range high elasticity Ni—Ti based alloy shown in Japanese Unexamined Patent Application Publication No. 2001-164348 or the like, and linear elastic Ni—Ti based alloy shown in Japanese Unexamined Patent Application Publication No. 2002-69555 or the like.

The Ni—Ti alloy or Ni—Ti based alloy having a pseudoelastic property is, for example, Ni—Ti alloy containing 48 at. % to 52 at. % of Ni and the balance Ti, Ni—Ti based alloy containing 48 at. % to 52 at. % of Ni, 0.05 at. % to 3.0 of one or two kinds selected from the group consisting of Cr, Fe, Co, Mo, V and Al and the balance Ti, or Ni—Ti based alloy containing 36.0 at. % to 48.0 at. % of Ni, 5.0 at. % to 12.0 at. % of Cu and the balance Ti.

For the second core 2B, martensitic stainless steel wire such as SUS403 and SUS410, ferritic stainless steel wire such as SUS405 and SUS430, or precipitation hardening stainless steel such as SUS630 and SUS631 are used, for example. In particular, austenitic stainless steel wire such as SUS304 and SUS316 having a strain-induced martensitic transformation phase in which a metamorphosing rate to a martensitic phase is increased by machining is suitable.

This is because the austenitic stainless steel wire has superior weldability compared to other stainless steel wires. Thus, the metamorphosing rate to the martensitic phase can be easily increased by machining by increasing a drawing rate of diameter reduction wire drawing (or total reduction of area) or the like. Hence, in addition to the tensile strength, the transverse elastic modulus which is an important technical element for improving the torsional rigidity can be increased.

Consequently, the rotation transmission performance can be improved from the second core 2B arranged at the proximal end side to the first core 2A arranged at the distal end side via the tubular connector 71.

For the tubular connector 71, Ni—Ti alloy or Ni—Ti based alloy having the above described pseudoelastic property is used. Alternatively, the martensitic stainless steel wire, the ferritic stainless steel wire, the precipitation hardening stainless steel, or the austenitic stainless steel is used for the tubular connector 71, for example.

When the first core 2A formed of the Ni—Ti alloy or the Ni—Ti based alloy or the like and the second core 2B formed of the stainless steel wire are welded and joined with the tubular connector 71, the tubular connector 71 is preferably formed of the Ni—Ti alloy or the Ni—Ti based alloy. From the viewpoint of the weldability, Ni—Cr—Fe alloy is preferred.

When the tubular connector 71 is adhered and joined both the first core 2A and the second core 2B, either one of the above described materials can be used.

In the connection structure of the connection portion 7 of the present invention, the important point for improving the rotation transmission performance from the proximal end side to the distal end side is to find out appropriate values of the torsional rigidity ratios between three members (first core 2A, second core 2B, tubular connector 71) from a large number of tests since the rotation transmission performance is significantly affected by the torsional rigidity of each member to be connected.

The coil body 3 is formed by winding a wire having a constant wire diameter t1 of 0.060 mm. In the coil body 3, an outer diameter A1 is 0.3556 mm and a length l2 is 50 mm to 100 mm.

For the coil body 3, the coil body 31 formed by winding a radioopaque wire containing tungsten, gold and platinum or a radioopaque wire containing doped tungsten, gold, platinum, nickel or the like is used at the distal end side, and the coil body 32 formed by winding a radiolucent wire of a stainless steel wire is used at the proximal end side. Alternatively, the coil body 3 can be formed by winding one radioopaque wire.

The lubricative coating 6 can be a coating using silicone oil or hydrophilic coating using hydrophilic substance which exhibits lubrication characteristics when wetted.

For the silicone oil, dimethylsilicone oil, methylphenyl silicone oil and reactive silicone oil can be used. The reactive silicone oil is preferably used.

This is because the reactive silicone oil has high adhesion to the metal wires (e.g., first core 2A, tubular connector 71, coil body 3).

For the hydrophilic substance of the hydrophilic coating, cellulosic high polymer substances such as a carboxymethyl cellulose, maleic anhydride high polymer substances such as a methyl vinyl ether-maleic anhydride copolymer, polyethylene oxide-based high polymer substances such as a polyethylene oxide and acrylamide-based high polymer substances such as a polyvinylpyrrolidone can be used, for example. A swelling ratio of the hydrophilic coating using the hydrophilic substance is 20% to 500%. (The swelling ratio is a percentage of a value obtained by subtracting a film thickness in a dry state from a film thickness in a swollen state.) As the swelling ratio increases (the thickness of an aqueous film of the hydrophilic substance becomes thicker), the film thickness of the hydrophilic coating increases and the slidability of the guide wire is improved to slide the guide wire without load.

In the connection portion 7, one end of the tubular connector 71 and the proximal end of the first core-large diameter proximal portion 21A are in contact with each other and connected and fixed to each other at least at the contact position. In addition, the other end of the tubular connector 71 and the distal end of the second core-large diameter portion 21B are in contact with each other and connected and fixed to each other at least at the contact position.

As for the portions and method to be connected and fixed, welding connection, brazing connection or adhesive connection can be used at a boundary position between the one end of the tubular connector 71 and the proximal end portion of the first core-large diameter proximal portion 21A and the tubular connector 71 over both the members. In addition, welding connection, brazing connection or adhesive connection can be used at a boundary position between the other end of the tubular connector 71 and the distal end portion of the second core-large diameter portion 21B over both the members.

As long as both the proximal end portion of the first core-large diameter proximal portion 21A and the distal end portion of the second core-large diameter portion 21B are connected and fixed to both ends of the tubular connector 71, the brazing connection or the adhesive connection can be used in a gap 8 formed between the inside of the tubular connector 71 and the small diameter proximal connection portion 27 or the small diameter distal connection portion 28. Alternatively, the brazing connection can be used between the outer periphery of one side of the tubular connector 71 and the outer periphery of the first small diameter proximal portion 27a and between the outer periphery of the other side of the tubular connector 71 and the outer periphery of the first small diameter distal portion 28a.

As for the method of connecting and fixing, one of or a combination of two or more of the welding connection, the brazing connection and the adhesive connection can be used.

For the welding connection, laser welding, resistance welding, and electron beam welding can be used, for example. For the brazing material of the brazing connection, a eutectic alloy is used as a joining member to connect the coil body 3 with the core 2. For the eutectic alloy, gold-tin based alloy material having a melting temperature of 210° C. to 450° C. and silver-tin based alloy material having a melting temperature of 220° C. to 470° C. are used.

For the adhesive connection, adhesive agents such as polyurethane based resin, epoxy based resin, acrylate based resin and urethane based resin are used, for example.

In the guide wire 1 of the present invention, the first core 2A arranged at the distal end side has a pseudoelastic property, the second core 2B arranged at the proximal end side has a strain-induced martensitic transformation phase, and the tubular connector 71 connects and fixes the proximal end portion of the first core 2A with the distal end portion of the second core 2B.

In the above described configuration, in order to improve the rotation transmission performance from the proximal end side to the distal end side, it is required to find out appropriate values of the torsional rigidity ratios between the members to be connected in the connection portion 7. Here, the members to be connected are the first core-large diameter proximal portion 21A of first core 2A, the tubular connector 71 and the second core-large diameter portion 21B.

In the connection structure formed by three members (first core 2A, second core 2B, tubular connector 71), if the value of the torsional rigidity of the member arranged at one side is high and the value of the torsional rigidity of the member arranged at the center portion is lower than the value of the torsional rigidities of the members arranged at the one side and the other side, the twist is unevenly generated at the center portion and the rotational force is hardly transferred to the distal end side even when the proximal end side is rotated.

In addition, the value of the torsional rigidity is largely affected not only by the peculiar elastic modulus possessed by the members but also by the structural difference (e.g., shape and dimensions) of the members.

This is because the torsional rigidity of the members can be expressed by a product of the transverse elastic modulus and the cross sectional second polar moment.

In the present invention, the torsional rigidity of each of the members is focused in the connection structure formed by three members. Thus, the torsional rigidity of each member is recognized and the correlation of the torsional rigidity ratios between three members are found out and specified from a large number of experiments. Consequently, the present invention relates to a technology for further improving the rotation transmission performance from the proximal end side to the distal end side.

For more details, when the torsional rigidity of the first core-large diameter proximal portion 21A of the first core 2A having a pseudoelastic property is defined as K1, the transverse elastic modulus is defined as G1 and the cross sectional second polar moment is defined as Ip1, since the outer diameter is D1, the cross sectional second polar moment Ip1 can be expressed by $(\pi \times D1^4/32)$ and the torsional rigidity K1 of the first core-large diameter proximal portion 21A can be expressed by the relational expression (1).

$$K1 = G1 \times (\pi \times D1^4/32) \tag{1}$$

When the torsional rigidity of the second core-large diameter portion 21B of the second core 2B having a strain-induced martensitic transformation phase is defined as K2, the transverse elastic modulus is defined as G2 and the cross sectional second polar moment is defined as Ip2, since the outer diameter is D2, same as the above described relational expression, the cross sectional second polar moment Ip2 can be expressed by $(\pi \times D2^4/32)$ and the torsional rigidity K2 of the second core-large diameter portion 21B can be expressed by the relational expression (2).

$$K2 = G2 \times (\pi \times D2^4/32) \tag{2}$$

When the torsional rigidity of the tubular connector 71 is defined as J1, the transverse elastic modulus is defined as G3 and the cross sectional second polar moment is defined as Ip3, since the outer diameter is do and the inner diameter is do1, the cross sectional second polar moment Ip3 can be expressed by $[\pi \times (do^4 - do1^4)/32]$ and the torsional rigidity J1 of the tubular connector 71 can be expressed by the relational expression (3).

$$J1 = G3 \times [\pi \times (do^4 - do1^4)/32] \tag{3}$$

From the above described relational expressions (1) and (3), the torsional rigidity ratio J1/K1 of the torsional rigidity J1 of the tubular connector 71 with respect to the torsional rigidity K1 of the first core-large diameter proximal portion 21A can be expressed by the relational expression (4).

$$J1/K1 = G3 \times (do^4 - do1^4)/(G1 \times D1^4) \tag{4}$$

(Here, the torsional rigidity ratio J1/K1 is a value calculated by dividing the torsional rigidity of the tubular connector 71 by the torsional rigidity of the first core-large diameter proximal portion 21A.)

In addition, from the above described relational expressions (1) and (2), the torsional rigidity ratio K2/K1 of the torsional rigidity K2 of the second core-large diameter portion 21B with respect to the torsional rigidity K1 of the first core-large diameter proximal portion 21A can be expressed by the relational expression (5).

$$K2/K1 = G2 \times D2^4/(G1 \times D1^4) \tag{5}$$

(Here, the torsional rigidity ratio K2/K1 is a value calculated by dividing the torsional rigidity of the second core-large diameter portion 21B by the torsional rigidity of the first core-large diameter proximal portion 21A.)

Here, the first core 2A arranged at the distal end side is a Ni—Ti alloy having a pseudoelastic property. The transverse elastic modulus G1 of the first core 2A is between 17650 Mpa and 21575 Mpa (average value: 19612.5 Mpa) when an austenite phase is exhibited at a temperature of 40° C.

When the tubular connector 71 is also the Ni—Ti alloy having the same pseudoelastic property as the first core 2A, since the transverse elastic modulus G3 is same as the transverse elastic modulus G1, the above described relational expression (4) can be expressed by the relational expression (6).

$$J1/K1 = (do^4 - do1^4)/D1^4 \tag{6}$$

In the first embodiment, since the outer diameter D1 of the first core-large diameter proximal portion 21A of the first core 2A is 0.312 mm, the outer diameter do of the tubular connector 71 is 0.356 mm and the inner diameter do1 is 0.256 mm, the torsional rigidity ratio J1/K1 of the torsional rigidity J1 of the tubular connector 71 with respect to the torsional rigidity K1 of the first core-large diameter proximal portion 21A is approximately 1.242 from the relational expression (6).

The second core 2B arranged at the proximal end side is an austenitic stainless steel wire having a strain-induced martensitic transformation phase by increasing the metamorphosing rate to the martensitic phase. The transverse elastic modulus G2 of the second core 2B is 68500 Mpa or more. Under a certain condition, an average value of the transverse elastic modulus G is 69000 Mpa. About the austenitic stainless steel wire having a strain-induced martensitic phase for improving the transverse elastic modulus by specifying the chemical abundance and the drawing rate will be described later.

In the first embodiment, when the outer diameter D1 of the first core-large diameter proximal portion 21A of the first core 2A is 0.312 mm, the transverse elastic modulus G1 is 19612.5 Mpa which is the average value, the outer diameter D2 of the second core-large diameter portion 21B of the second core 2B is 0.340 mm and the transverse elastic modulus G2 is 69000 Mpa which is the average value, the torsional rigidity ratio K2/K1 of the torsional rigidity K2 of the second core-large diameter portion 21B with respect to the torsional rigidity K1 of the first core-large diameter proximal portion 21A is approximately 4.962 from the relational expression (5).

The torsional rigidity ratio J1/K1 of the torsional rigidity J1 of the tubular connector 71 with respect to the torsional rigidity K1 of the first core-large diameter proximal portion 21A is approximately 1.242. The torsional rigidity ratio K2/K1 of the torsional rigidity K2 of the second core-large diameter portion 21B with respect to the torsional rigidity K1 of the first core-large diameter proximal portion 21A is approximately 4.962. When the torsional rigidity K1 of the first core-large diameter proximal portion 21A is 1, the correlation between the torsional rigidity ratios J1/K1 and K2/K1 can be expressed by the relational expression (7).

$$(K2/K1) > (J1/K1) > 1 \tag{7}$$

The relational expression (7) means that the torsional rigidity ratio is increased from the distal end side to the proximal end side.

In the connection structure formed by three members: the first core 2A; the second core 2B; and the tubular connector 71, when the torsional rigidity ratios between the members satisfy the relation of the above described relational expression (7), the rotation transmission performance from the proximal end side to the distal end side can be improved.

For example, when the torsional rigidity ratio J1/K1 is below 1 in the relational expression (7), flexural deformation is caused and the twist is unevenly generated between the second core-large diameter portion 21B located at the proximal end side and the first core-large diameter proximal portion 21A located at the distal end side. Because of this, the rotational force of the proximal end side is hardly transferred to the distal end side. If the rotational force is further strongly applied, buckling deformation is caused and it becomes impossible to transfer the rotational force to the distal end side.

The same problems occur when the torsional rigidity ratio K2/K1 is below 1. Furthermore, when the magnitude relation between the torsional rigidity ratio K2/K1 and the torsional rigidity ratio J1/K1 is reversed [(K2/K1)>(J1/K1)], same problems occur.

Accordingly, in order to improve the rotation transmission performance from the proximal end side to the distal end side, in addition to the relation of the rigidity possessed by two materials: the second core-large diameter portion 21B located at the proximal end side; and the first core-large diameter proximal portion 21A located at the distal end side, it is important that the correlation of the torsional rigidity ratios between the three members including the tubular connector 71 satisfies the relational expression (7).

From a large number of experiments, a preferable correlation of the torsional rigidity ratios between the three members is to satisfy the relational expression (8).

$$5.85 \geq (K2/K1) > (J1/K1) > 1 \quad (8)$$

When the torsional rigidity ratio K2/K1, which is one of the torsional rigidity ratios, exceeds the upper limit value of the above described relational expression (8), the difference of the torsional rigidity between the torsional rigidity K1 of the first core-large diameter proximal portion 21A and the torsional rigidity K2 of the second core-large diameter portion 21B is increased. Because of this, flexibility deteriorates in inverse proportion to increase of the torsional rigidity K2 of the second core-large diameter portion 21B. Consequently, frictional resistance between the second core-large diameter portion 21B and the blood vessel wall in the bent and meandered blood vessel is increased, and the rotation transmission performance to the distal end side is rather deteriorated.

More preferably, both the following relational expressions are satisfied.

$$5.65 \geq (K2/K1) > (J1/K1) > 1 \text{ and}$$

$$4.48 \geq (J1/K1)$$

Figure 3:
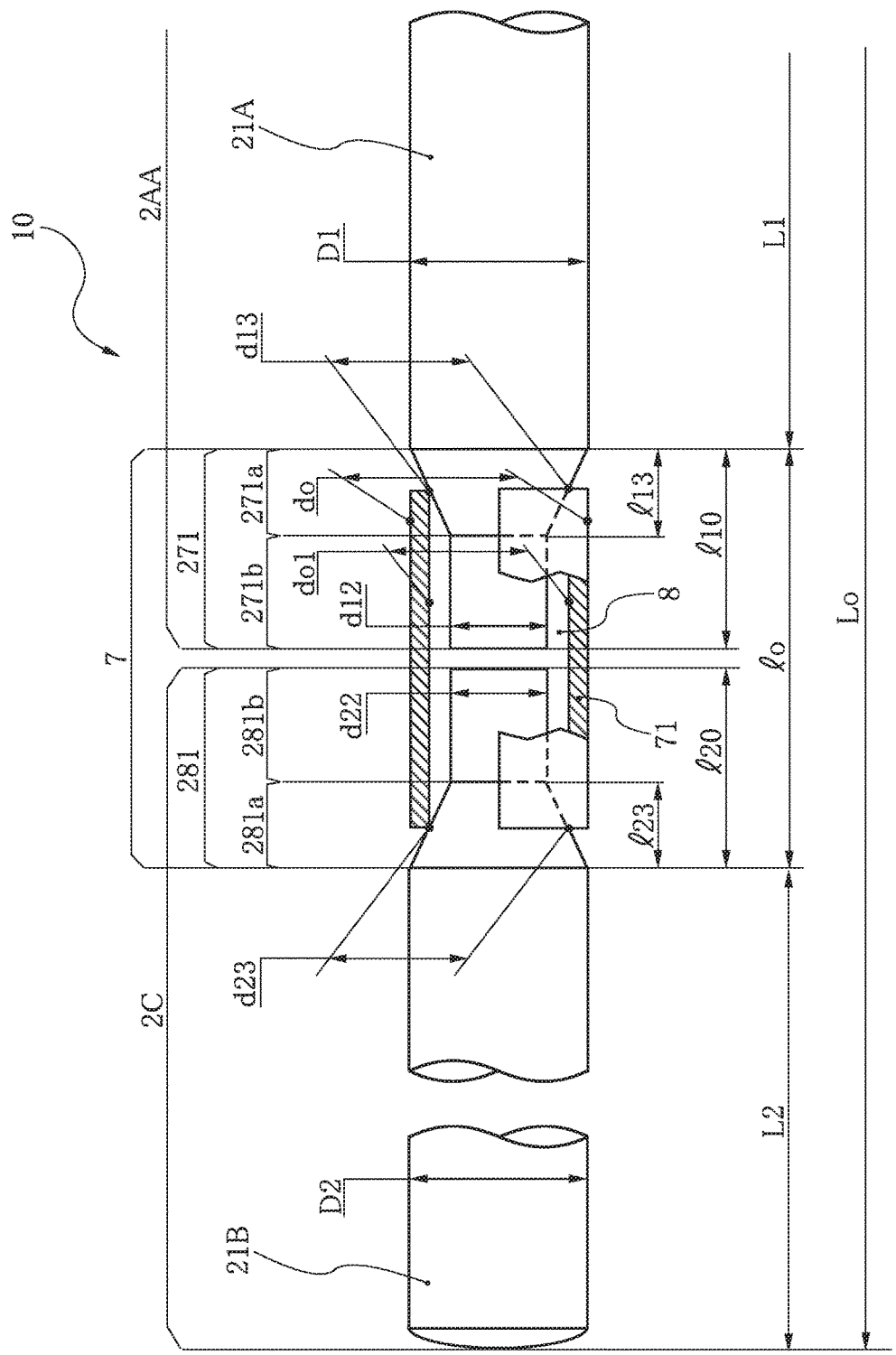
FIG. 3 is an enlarged partially cutaway side view of a main part of a connection portion concerning the second embodiment of the present invention.

FIG. 3 shows a guide wire 10 concerning the second embodiment of the present invention. Same as FIG. 2, FIG. 3 shows a main part of the connection portion 7. The difference from the first embodiment is the connection structure between the cores (first core 2AA, second core 2C) and the tubular connector 71 in the connection portion 7. Note that the fluorocarbon polymer coating 5 and the lubricative coating 6 are omitted. These are omitted also in the later explained FIG. 4 and FIG. 5.

Same as the first embodiment, in the guide wire 10 of the present invention, the first core 2AA arranged at the distal end side has a pseudoelastic property, the second core 2C arranged at the proximal end side has a strain-induced martensitic transformation phase, and the tubular connector 71 connects and fixes the proximal end portion of the first core 2AA with the distal end portion of the second core 2C.

The first core 2AA has a first core-large diameter proximal portion 21A having an outer diameter D1 of 0.312 mm and a small diameter proximal connection portion 271 having a length l10 of 19 mm.

The small diameter proximal connection portion 271 has a first small diameter proximal portion 271a and a second small diameter proximal portion 271b located at the distal end side. The first small diameter proximal portion 271a has a length l13 of 4 mm and has a tapered portion. An outer diameter of tapered portion is gradually reduced from 0.312 mm to 0.220 mm. The second small diameter proximal portion 271b has a constant outer diameter d12 of 0.220 mm.

The second core 2C has a second core-large diameter portion 21B having an outer diameter D2 of 0.340 mm and a small diameter distal connection portion 281 having a length l20 of 19 mm.

The small diameter distal connection portion 281 has a first small diameter distal portion 281a and a second small diameter distal portion 281b located at the distal end side. The first small diameter distal portion 281a has a length l23 of 4 mm and has a tapered portion. An outer diameter of the tapered portion is gradually reduced from 0.340 mm to 0.220 mm. The second small diameter distal portion 281b has a constant outer diameter d22 of 0.220 mm.

Same as the first embodiment, in the tubular connector 71, a length lo is 35 mm, an outer diameter d0o is 0.356 mm and an inner diameter do1 is 0.256 mm.

The second small diameter proximal portion 271b and the first small diameter proximal portion 271a are inserted into the tubular connector 71 from one side of the tubular connector 71 to the position of the depth of the hole of 17 mm, and the second small diameter distal portion 281b and the first small diameter distal portion 281a are inserted into the tubular connector 71 from the other side of the tubular connector 71 to the position of the depth of the hole of 17 mm.

An inner end portion of one side of the tubular connector 7b is in contact with an approximately center position of the tapered portion of the first small diameter proximal portion 271a, and an outer diameter d13 of the contact position is 0.256 mm which is same as the inner diameter of the tubular connector 71. In addition, an inner end portion of the other side of the tubular connector 7b is in contact with an approximately center position of the tapered portion of the first small diameter distal portion 281a, and an outer diameter d23 of the contact position is 0.256 mm which is same as the inner diameter of the tubular connector 71.

In the connection portion 7, the inner end portion of one side of the tubular connector 71 and the tapered portion of the first small diameter proximal portion 271a are in contact with each other and connected and fixed to each other at least at the contact position. In addition, the inner end portion of the other side of the tubular connector 71 and the tapered portion of the first small diameter distal portion 281a are in contact with each other and connected and fixed to each other at least at the contact position.

The portion to be connected and fixed is at least the contact position. The method to connect and fix is welding connection, brazing connection or adhesive connection over both the contact portions.

Same as the first embodiment, as long as the first small diameter proximal portion 271a (i.e., contact end) of the small diameter proximal connection portion 271 of the first core 2AA and the first small diameter distal portion 281a (i.e., contact end) of the small diameter distal connection portion 281 of the second core 2C are connected and fixed to both ends of the tubular connector 71, the brazing connection or the adhesive connection can be used in a gap 8 formed between the inside of the tubular connector 71 and the small diameter proximal connection portion 271 or the small diameter distal connection portion 281. Alternatively, the brazing connection can be used between the outer periphery of one side of the tubular connector 71 and the small diameter proximal connection portion 271 and between the outer periphery of the other side of the tubular connector 71 and the small diameter distal connection portion 281.

Same as the first embodiment, one of or a combination of two or more of the welding connection, the brazing connection and the adhesive connection can be used as the method to connect and fix.

The welding connection, the brazing connection and the adhesive connection are same as the first embodiment.

In FIG. 3, the rotation is transmitted from the second core 2C arranged at the distal end side to the tubular connector 71, and then transmitted from the tubular connector 71 to the first core 2AA. Thus, the rotation is transmitted from the proximal end side to the distal end side in the connection portion 7. In this case, the transmission of the rotation from the second core 2C to the tubular connector 71 is transmitted to the end portion of the proximal end side of the tubular connector 71 via the first small diameter distal portion 281a (tapered portion) which is the contact end between the second core 2C and the tubular connector 71.

Then, the rotation transmitted to the end portion of the proximal end side of the tubular connector 71 is transmitted to the first small diameter proximal portion 271*a* (tapered portion) via the end portion of the distal end side of the tubular connector 71. Here, the end portion of the distal end side is the contact end between the first core 2AA and the tubular connector 71.

Accordingly, in the transmission of the rotation from the proximal end side to the distal end side, the correlation of the torsional rigidity of the contact end between the first small diameter distal portion 281 and the tubular connector 71, the torsional rigidity of the tubular connector 71, and the torsional rigidity of the contact end between the first small diameter proximal portion 271*a* and the tubular connector 71 are important.

The torsional rigidities of the contact ends between the first small diameter distal portion 281*a* and the tubular connector 71 and between the first small diameter proximal portion 271*a* and the tubular connector 71 are important because high torsional stress is applied to the position of the contact ends by the rotation.

This is same also in the first embodiment. In the first embodiment, the contact ends between the second core-large diameter portion 21B and the tubular connector 71 and between the first core-large diameter proximal portion 21A and the tubular connector 71 are the position to which high torsional stress is applied by the rotation.

The outer diameter d13 of the first small diameter proximal portion 271*a* of the first core 2AA at the contact end with respect to the tubular connector 71 is 0.256 mm. The outer diameter d23 of the first small diameter distal portion 281*a* of the second core 2C at the contact end with respect to the tubular connector 71 is 0.256 mm.

When the torsional rigidity of the small diameter proximal connection portion 271 of the first core 2AA having a pseudoelastic property is defined as k11 and the cross sectional second polar moment is defined as Ip11, since the transverse elastic modulus is G1 same as the first core-large diameter proximal portion 21A and the outer diameter at the contact end with respect to the tubular connector 71 is d13, the cross sectional second polar moment Ip11 can be expressed by $(\pi \times d13^4/32)$ and the torsional rigidity k11 of the small diameter proximal connection portion 271 can be expressed by the relational expression (9).

$$k11 = G1 \times (\pi \times d13^4/32) \quad (9)$$

When the torsional rigidity of the small diameter distal connection portion 281 of the second core 2C having a strain-induced martensitic transformation phase is defined as k22 and the cross sectional second polar moment is defined as Ip22, since the transverse elastic modulus is G2 same as the second core-large diameter portion 21B and the outer diameter of the contact end with respect to the tubular connector 71 is d23, the cross sectional second polar moment Ip22 can be expressed by $(\pi \times d23^4/32)$ and the torsional rigidity k22 of the small diameter distal connection portion 281 can be expressed by the relational expression (10).

$$k22 = G2 \times (\pi \times d23^4/32) \quad (10)$$

The torsional rigidity ratio J1/k11 of the torsional rigidity J1 of the tubular connector 71 with respect to the torsional rigidity k11 of the small diameter proximal connection portion 271 can be expressed by the relational expression (11) from the relational expressions (3) and (9).

$$J1/k11 = G3 \times (do^4 - do1^4)/(G1 \times d13^4) \quad (11)$$

(Here, the torsional rigidity ratio J1/k11 is a value calculated by dividing the torsional rigidity of the tubular connector by the torsional rigidity of the small diameter proximal connection portion.)

The torsional rigidity ratio k22/k11 of the torsional rigidity k22 of the small diameter distal connection portion 281 with respect to the torsional rigidity k11 of the small diameter proximal connection portion 271 can be expressed by the relational expression (12) from the relational expressions (9) and (10).

$$k22/k11 = G2 \times d23^4/(G1 \times d13^4) \quad (12)$$

(Here, the torsional rigidity ratio k22/k11 is a value calculated by dividing the torsional rigidity of the small diameter distal connection portion by the torsional rigidity of the small diameter proximal connection portion.)

Since the first core 2AA having a pseudoelastic property and arranged at the distal end side has the same transverse elastic modulus as the first core 2A of the first embodiment, the transverse elastic modulus is G1. Furthermore, when the tubular connector 71 is same as the first embodiment, the transverse elastic modulus G3 is same as the transverse elastic modulus G1. Thus, the above described relational expression (11) can be expressed by the relational expression (13).

$$J1/k11 = (do^4 - do1^4)/d13^4 \quad (13)$$

In the second embodiment, the outer diameter d13 of the small diameter proximal connection portion 271 of the first core 2AA at the contact end with respect to the tubular connector 71 is 0.256 mm, the outer diameter d0*o* of the tubular connector 71 is 0.356 mm and the inner diameter do1 is 0.256 mm, the torsional rigidity ratio J1/k11 of the torsional rigidity J1 of the tubular connector 71 with respect to the torsional rigidity k11 of the small diameter proximal connection portion 271 is approximately 2.740 from the relational expression (13).

The second core 2C having a strain-induced martensitic transformation phase and arranged at the proximal end side has the same transverse elastic modulus as the second core 2B of the first embodiment, the transverse elastic modulus is G2.

In the second embodiment, when the outer diameter d13 of the small diameter proximal connection portion 271 of the first core 2AA at the contact end with respect to the tubular connector 71 is 0.256 mm, the transverse elastic modulus G1 is 19612.5 Mpa which is the average value, the outer diameter d23 of the small diameter distal connection portion 281 of the second core 2C at the contact end with respect to the tubular connector 71 is 0.256 mm, and the transverse elastic modulus G2 is 69000 Mpa which is the average value, the torsional rigidity ratio k22/k11 of the torsional rigidity k22 of the small diameter distal connection portion 281 with respect to the torsional rigidity k11 of the small diameter proximal connection portion 271 is approximately 3.518 from the relational expression (12).

The torsional rigidity ratio J1/k11 of the torsional rigidity J1 of the tubular connector 71 with respect to the torsional rigidity k11 of the small diameter proximal connection portion 271 is approximately 2.740. The torsional rigidity ratio k22/k11 of the torsional rigidity J1 of the small diameter distal connection portion 281 with respect to the torsional rigidity k11 of the small diameter proximal connection portion 271 is approximately 3.518. When the torsional rigidity k11 of the small diameter proximal connection portion 271 is 1, the correlation between the torsional rigidity ratios J1/k11 and k22/k11 can be expressed by the relational expression (14).

$$(k22/k11)>(J1/k11)>1 \qquad (14)$$

Same as the relational expression (7), the relational expression (14) means that the torsional rigidity ratio is gradually increased from the distal end side to the proximal end side.

In the connection structure formed by three members: the first core 2AA; the second core 2C; and the tubular connector 71, when the torsional rigidity ratios between the members satisfy the relation of the above described relational expression (14), the rotation transmission performance from the proximal end side to the distal end side can be improved.

Same as the first embodiment, for example, when the torsional rigidity ratio J1/k11 is below 1 in the relational expression (14), flexural deformation is caused and the twist is unevenly generated between the small diameter distal connection portion 281 located at the proximal end side and the small diameter proximal connection portion 271 located at the distal end side. Because of this, the rotational force of the proximal end side is hardly transferred to the distal end side. If the rotational force is further strongly applied, buckling deformation is caused and it becomes impossible to transfer the rotational force to the distal end side.

The same problems occur when the torsional rigidity ratio k22/k11 is below 1. Furthermore, when the magnitude relation between the torsional rigidity ratio k22/k11 and the torsional rigidity ratio J1/k11 is reversed [(k22/k11)<(J1/k11)], same problems occur.

Accordingly, in order to improve the rotation transmission performance from the proximal end side to the distal end side, in addition to the relation of the rigidity possessed by two materials: the second core-large diameter portion 21B of the second core 2C located at the proximal end side and the first core-large diameter proximal portion 21A of the first core 2AA located at the distal end side, it is important especially in the second embodiment that the correlation of the torsional rigidity ratios between the three members: the small diameter proximal connection portion 271 of the first core 2AA; the small diameter distal connection portion 281 of the second core 2C; and the tubular connector 71 satisfies the relational expression (14). Here, the small diameter proximal connection portion 271 of the first core 2AA and the small diameter distal connection portion 281 of the second core 2C are both contact ends with respect to the tubular connector 71.

From a large number of experiments, a preferable correlation of the torsional rigidity ratios between the three members is to satisfy the relational expression (15).

$$5.85 \geq (k22/k11)>(J1/k11)>1 \qquad (15)$$

Same as the first embodiment, when one of the torsional rigidity ratio k22/k11, which is one of the torsional rigidity ratios, exceeds the upper limit value of the above described relational expression (15), the difference of the torsional rigidity between the torsional rigidity k11 of the small diameter proximal connection portion 271 and the torsional rigidity k22 of the small diameter distal connection portion 281 is increased. Because of this, flexibility deteriorates in inverse proportion to increase of the torsional rigidity k22 of the small diameter distal connection portion 281. Consequently, frictional resistance between the second core-large diameter portion 21B and the blood vessel wall in the bent and meandered blood vessel is increased, and the rotation transmission performance to the distal end side is rather deteriorated.

A large number of experiments was carried out about the torsional rigidity ratios between the three members: the tubular connector 71; the small diameter proximal connection portion 271 which is the contact end to the tubular connector 71; and the small diameter distal connection portion 281 which is the contact end to the tubular connector 71 in the viewpoint of the slidability in addition to the rotation transmission performance. After the result of the experiments was analyzed, a more preferable correlation of the torsional rigidity ratios satisfies the relational expression (16).

$$4.85 \geq (k22/k11)>(J1/k11)>1 \text{ and}$$

$$3.40 \geq (J1/k11) \qquad (16)$$

Further more preferably, the correlation of the torsional rigidity ratios satisfies the relational expression (17).

$$4.50 \geq (k22/k11)>(J1/k11) \text{ and}$$

$$3.20 \geq (J1/k11) \geq 1.20 \qquad (17)$$

In the second core 2B and the second core 2C of the first and second embodiments, in order to obtain the austenitic stainless steel wire having the strain-induced martensitic transformation phase in which the metamorphosing rate to the martensitic phase is increased by machining, the drawing rate of the wire drawing should be increased, the chemical abundance of the wire for the wire drawing should be specified, or a low temperature annealing treatment should be applied. One of the above described operations can used alone or two or more above described operations can be used in combination. (Here, the drawing rate also means a total reduction rate which indicates a rate between the diameter before applying the wire drawing and the diameter after applying the final wire drawing when the wire drawing and thermal treatment are repeated a plurality of times. Hereafter, the drawing rate including the total reduction rate is referred to as merely the drawing rate.)

As an example of increasing the drawing rate of the wire drawing, the wire subjected to a solid solution heat treatment is processed in the drawing rate of the wire drawing of between 70% and 99.6% (70% or more and 99.6% or less). As an example of specifying the chemical abundance of the wire for the wire drawing, when the austenitic stainless steel wire SUS304 is used, an addition amount of Ni and Cr is specified to be near the lower limit value defined in the JIS standard. With respect to the standard value of Ni of 8.00% to 10.50%, the value of 8.00% to 8.20% is used. With respect to the standard value of Cr of 18.00% to 20.00%, the value of 18.00% to 18.20% is used. Alternatively, 8.00% to 8.20% for Ni and 18.00% to 18.20% for Cr are used.

As an example of using them in combination, the wire formed by specifying the chemical abundance is used and the wire drawing is applied with the drawing rate of between 70% and 99.6%.

After the final wire drawing is applied, the low temperature annealing treatment (360° C. to 480° C.) is applied with the above described drawing rate.

By using one of the above described operations or combining two or more above described operations, the metamorphosing rate to the strain-induced martensitic phase by machining is specified to be between 20% and 80% (20% or more and 80% or less). When the drawing rate is between 70% and 85% (70% or more and 85% or less), the transverse elastic modulus of 65000 Mpa can be increased to between 68500 Mpa and 69500 Mpa (average value: 69000 Mpa).

When the drawing rate is between 85% and 96% (85% or more and 99.6% or less) and the low temperature annealing treatment is applied after the final wire drawing, the transverse elastic modulus can be increased to 73000 Mpa exceeding 69500 Mpa.

The above described explanation can be also applied to SUS304 base such as SUS304H and 304L, SUS301 base, SUS302 base, and SUS303 base. In addition, it can be also applied to SUS316 base such as SUS316 and SUS316L containing Mo.

By using both the above described drawing rate and the low temperature annealing treatment using the wire formed by specifying the chemical abundance, the austenitic stainless steel wire having high and stable transverse elastic modulus can be obtained.

In the second core 2B and the second core 2C of the first and second embodiments, the average value of 69000 Mpa is used for the transverse elastic modulus G2 when calculating the torsional rigidity ratios between the three members of the connection portion 7. When calculating the upper limit values of the torsional rigidity ratios (K2/K1, k22/k11), the maximum value of 73000 Mpa is taken into consideration.

Figure 4:
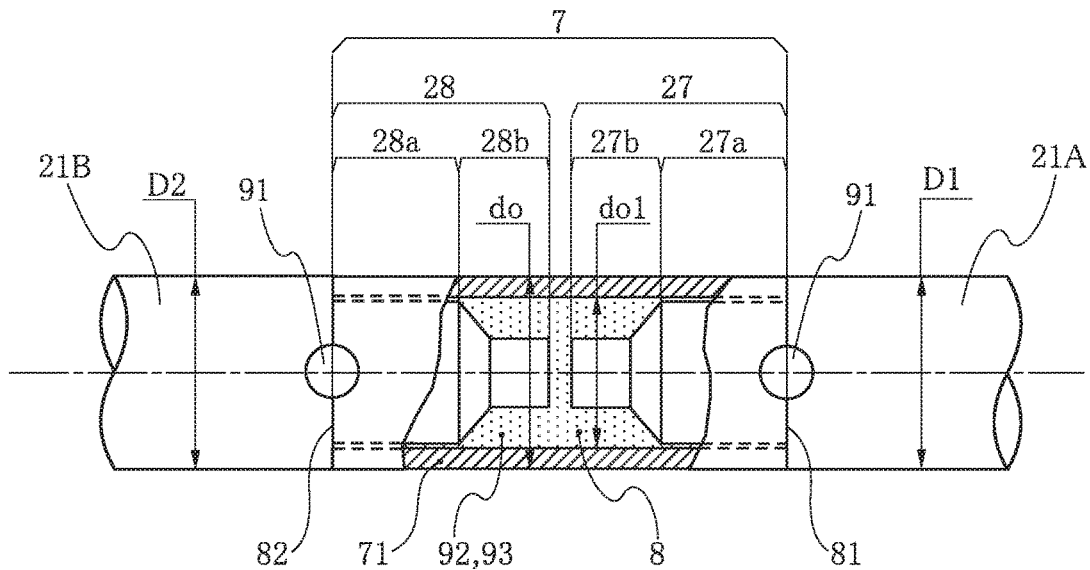
FIG. 4 is an enlarged partially cutaway side view of a main part for explaining the connection and fixing of the connection portion concerning the first embodiment of the present invention.

FIG. 4 is an explanation drawing for more specifically explaining the connection and the fixing between the tubular connector 71 and the first core-large diameter proximal portion 21A and between the tubular connector 71 and the second core-large diameter portion 21B in the connection portion 7 concerning the first embodiment.

A boundary position where one end of the tubular connector 71 and the proximal end of the first core-large diameter proximal portion 21A are in contact with each other is shown by a reference sign 81. The other boundary position where the other end of the tubular connector 71 and the second core-large diameter portion 21B are in contact with each other is shown by a reference sign 82.

The connection and the fixing in the first embodiment mean that one end of the tubular connector 71 and the proximal end of the first core-large diameter proximal portion 21A are connected and fixed to each other and the other end of the tubular connector 71 and the second core-large diameter portion 21B are connected and fixed to each other at least at the boundary positions 81, 82.

The method of the connection and the fixing at the boundary positions 81, 82 is the welding connection (reference sign 91), the brazing connection (reference sign 92) and the adhesive connection (reference sign 93).

As long as the above described both portions are connected and fixed to each other at the boundary positions 81, 82, the brazing connection (reference sign 92) or the adhesive connection (reference sign 93) can be used in the gap 8. The welding connection between the outer periphery of one side of the tubular connector 71 and the outer periphery of the first small diameter proximal portion 27a of the first core 2A and the welding connection between the outer periphery of the other side of the tubular connector 71 and the first small diameter distal portion 28a of the second core 2B can be the welding connection (reference sign 91) as shown in the next FIG. 5.

Figure 5:
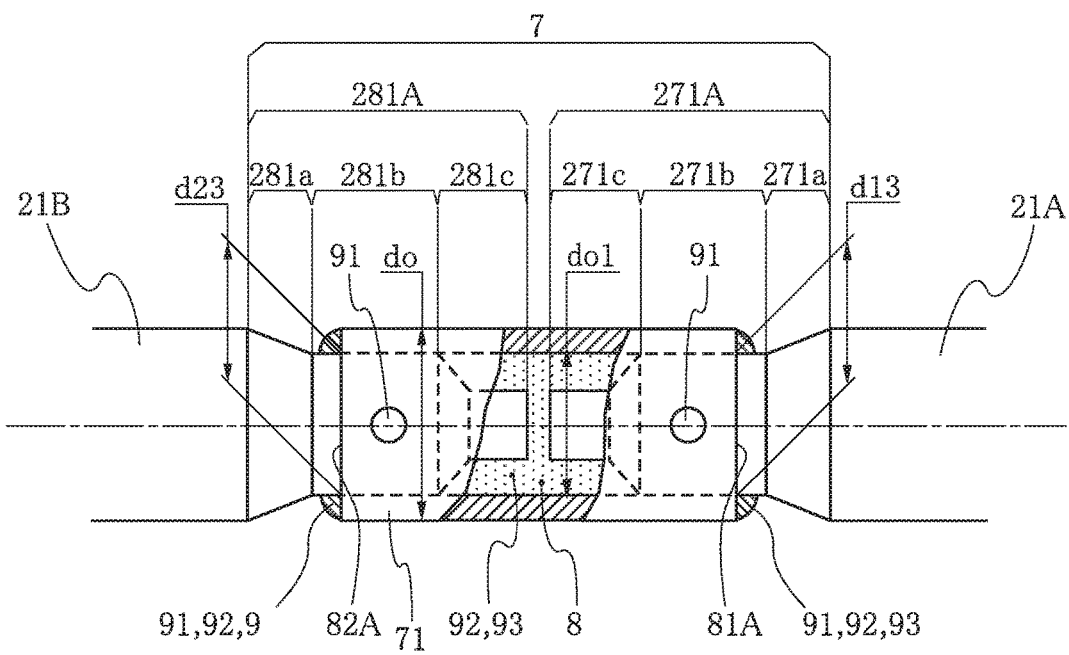
FIG. 5 is an enlarged partially cutaway side view of a main part for explaining the connection and fixing of the connection portion in the variation example concerning the second embodiment of the present invention.

FIG. 5 is an explanation drawing of the variation example of the second embodiment in the connection portion 7.

A small diameter proximal connection portion 271A includes a first small diameter proximal portion 271a having a tapered portion, a second small diameter proximal portion 271b having a constant diameter, and a protruded proximal portion 271c.

A small diameter distal connection portion 281A includes a first small diameter distal portion 281a having a tapered portion, a second small diameter distal portion 281b having a constant diameter, and a protruded distal portion 281c.

In the connection portion 7, one side of the tubular connector 71 is connected and fixed to the second small diameter proximal portion 271b, the other side of the tubular connector 71 is connected and fixed to the second small diameter distal portion 281b.

The connection and the fixing in the variation example of the second embodiment mean that the outer periphery of one side of the tubular connector 71 and the second small diameter proximal portion 271b are connected and fixed to each other and the outer periphery of the other side of the tubular connector 71 and the second small diameter distal portion 281b are connected and fixed to each other at least at both end sides of the tubular connector 71.

The connection and the fixing are the welding connection (reference sign 91) between the outer periphery of one side of the tubular connector 71 and the second small diameter proximal portion 271b and the welding connection (reference sign 91) between the outer periphery of the other side of the tubular connector 71 and the second small diameter distal portion 281b.

The connection and the fixing to the second small diameter proximal portion 271b and the second small diameter distal portion 281b at the boundary positions 81A, 82A are the welding connection (reference sign 91), the brazing connection (reference sign 92) and the adhesive connection (reference sign 93).

Same as the above described embodiments, as long as the both portions are connected and fixed to each other at least at both ends of the tubular connector 71 or the boundary positions 81A, 82A, the brazing connection (reference sign 92) or the adhesive connection (reference sign 93) can be used in the gap 8.

In the variation example of the second embodiment, when calculating the torsional rigidity ratios between the members of the connection structure formed by three members, the outer diameter d13 of the connection end connected to the tubular connector 71 is used for calculating the torsional rigidity of the small diameter proximal connection portion 271A and the outer diameter d23 of the connection end connected to the tubular connector 71 is used for calculating the torsional rigidity of the small diameter distal connection portion 281A.

This is because both connection ends are the position where high torsional stress is applied by the rotation, same as the first and second embodiments.

Figure 6:
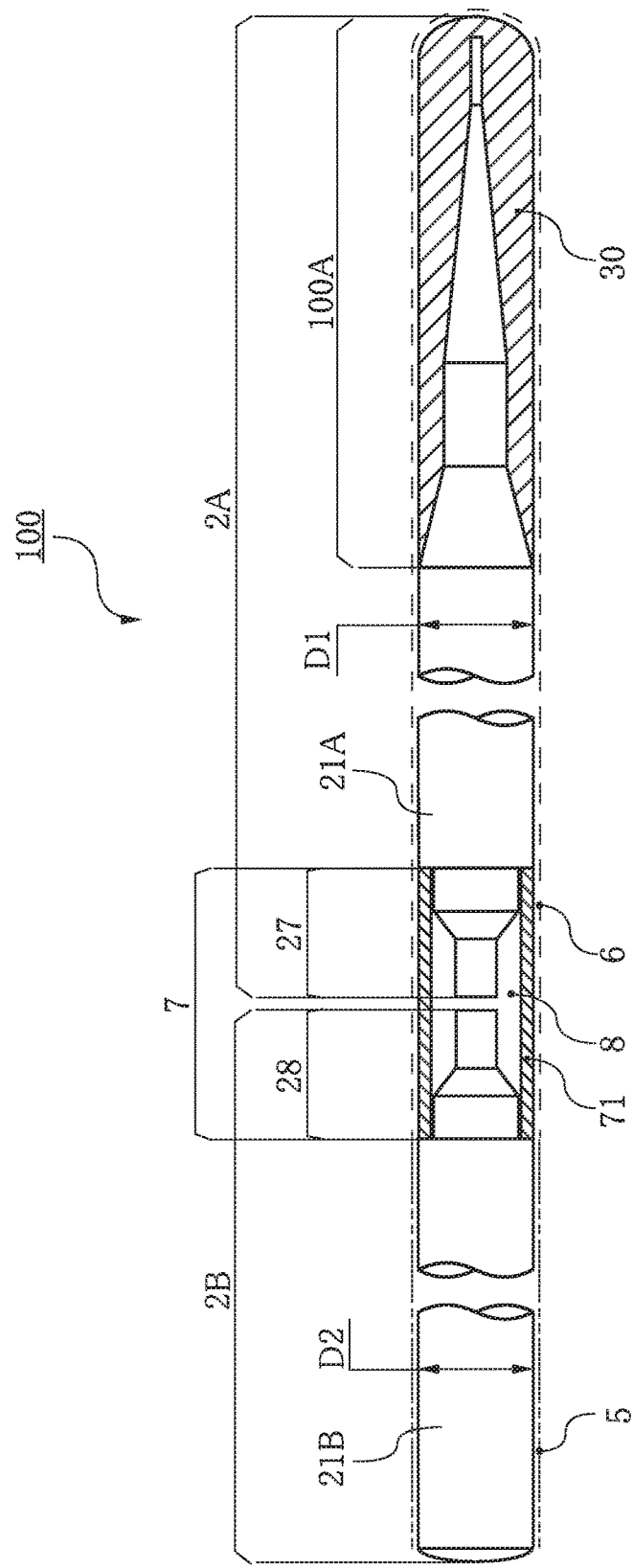
FIG. 6 is an enlarged partially cutaway side view showing whole a guide wire concerning the third embodiment of the present invention.

FIG. 6 shows a guide wire 100 of the third embodiment. The differences from the first and second embodiments are that a distal end side 100A is provided in a state that a synthetic resin coating 30 is formed on the outer side of the distal end side 100A. In addition, the coil body 3, the distal joining portion 4a and the proximal joining portion 4b are not provided. Furthermore, the lubricative coating 6 is formed on the outer periphery of the synthetic resin coating 30. Except for the above described differences, the third embodiment is same as the first and second embodiments. Note that the connection portion 7 has one of the connection structures of the connection portion 7 described in the first embodiment and the second embodiment.

Because of this, even when the guide wire 100 in which the synthetic resin coating 30 is formed instead of the coil body 3 of the distal end side is used, the same operation and effect as the first and second embodiments can be achieved.

For the synthetic resin coating 30, polyurethane resin, polyamide resin, polyethylene resin and fluorine resin are used, for example.

In the connection structure of the connection portion 7 of the first and second embodiments, the explanation is made on condition that the value of the transverse elastic modulus G1 of the first cores 2A, 2AA is same as the value of the transverse elastic modulus G3 of the tubular connector 71. However, when these values are different, the correlation of the torsional rigidity ratios between the members is as follows. Note that the reference signs of the main components are added in brackets.

In the case of the first embodiment, a medical guide wire comprising a first core (2A), a second core (2B) and a tubular connector (71), wherein a proximal end of the first core (2A) and a distal end of a second core (2B) are connected and fixed to each other by the tubular connector (71), the first core (2A) has a pseudoelastic property and includes a small diameter proximal connection portion (27) and a first core-large diameter proximal portion (21A) in order from the proximal end to the distal end, the second core (2B) has a strain-induced martensitic transformation phase and includes a second core-large diameter portion (21B) and a small diameter distal connection portion (28) in order from the proximal end to the distal end, the small diameter proximal connection portion (27) is inserted into the tubular connector (71) from one side of tubular connector (71) and the small diameter distal connection portion (28) is inserted into the tubular connector (71) from the other side of the tubular connector (71), the tubular connector (71) at least connects and fixes the first core-large diameter proximal portion (21A) located at one side of the tubular connector (71) with the second core-large diameter portion (21B) located at the other side of the tubular connector (71), when the torsional rigidity of the first core-large diameter proximal portion (21A) is defined as K1, the transverse elastic modulus is defined as G1, the cross sectional second polar moment is defined as Ip1 and the outer diameter is defined as D1, the cross sectional second polar moment Ip1 can be expressed by $(\pi \times D1^4/32)$ and the torsional rigidity K1 of the first core-large diameter proximal portion (21A) can be expressed by $G1 \times (\pi \times D1^4/32)$, when the torsional rigidity of the second core-large diameter portion (21B) is defined as K2, the transverse elastic modulus is defined as G2, the cross sectional second polar moment is defined as Ip2 and the outer diameter is defined as D2, the cross sectional second polar moment Ip2 can be expressed by $(\pi \times D2^4/32)$ and the torsional rigidity K2 of the second core-large diameter portion (21B) can be expressed by $G2 \times (\pi \times D2^4/32)$, when the torsional rigidity of the tubular connector (71) is defined as J1, the transverse elastic modulus is defined as G3, the cross sectional second polar moment is defined as Ip3, the outer diameter is defined as do and the inner diameter is defined as do1, the cross sectional second polar moment Ip3 can be expressed by $[\pi \times (do^4 - do1^4)/32]$ and the torsional rigidity J1 of the tubular connector (71) can by expressed by $G3 \times [\pi \times (do^4 - do1^4)/32]$, and the relational expression $(K2/K1) > (J1/K1) > 1$ between the torsional rigidity ratio (J1/K1) of the torsional rigidity J1 of the tubular connector (71) with respect to the torsional rigidity K1 of the first core-large diameter proximal portion (21A) and the torsional rigidity ratio (K2/K1) of the torsional rigidity K2 of the second core-large diameter portion (21B) with respect to the torsional rigidity K1 of the first core-large diameter proximal portion (21A) satisfies the following relational expression from the above described relational expressions (4) (5).

$$[G2 \times D2^4/(G1 \times D1^4)] > [G3 \times (do^4 - do1^4)/(G1 \times D1^4)] > 1$$

Preferably, the following relational expression is satisfied.

$$5.85 \geq [G2 \times D2^4/(G1 \times D1^4)] > [G3 \times (do^4 - do1^4)/(G1 \times D1^4)] > 1$$

More preferably, the following relational expressions are satisfied.

$$5.65 \geq [G2 \times D2^4/(G1 \times D1^4)] > [G3 \times (dp4 - do1^4)/(G1 \times D1^4)] > 1 \text{ and}$$

$$4.48 \geq [G3 \times (do^4 - do1^4)/(G1 \times D1^4)]$$

In the case of the second embodiment, a medical guide wire comprising a first core (2AA), a second core (2C) and a tubular connector (71), wherein a proximal end of the first core (2AA) and a distal end of a second core (2C) are connected and fixed to each other by the tubular connector (71), the first core (2AA) has a pseudoelastic property and includes a small diameter proximal connection portion (271) and a first core-large diameter proximal portion (21A) in order from the proximal end to the distal end, the second core (2C) has a strain-induced martensitic transformation phase and includes a second core-large diameter portion (21B) and a small diameter distal connection portion (281) in order from the proximal end to the distal end, the small diameter proximal connection portion (271) is inserted into the tubular connector (71) from one side of tubular connector (71) and the small diameter distal connection portion (281) is inserted into the tubular connector (71) from the other side of the tubular connector (71), the tubular connector (71) at least connects and fixes the small diameter proximal connection portion (271) located at one side of the tubular connector (71) with the small diameter distal connection portion (281) located at the other side of the tubular connector (71), when the torsional rigidity of the small diameter proximal connection portion (271) is defined as k11, the transverse elastic modulus is defined as G1 same as the first core-large diameter proximal portion (21A), the cross sectional second polar moment is defined as Ip11, the transverse elastic modulus is defined as D1 same as the above, and the outer diameter of the contact end to the tubular connector (71) is defined as d13, the cross sectional second polar moment Ip11 can be expressed by $(\pi \times d13^4/32)$ and the torsional rigidity k11 of the small diameter proximal connection portion (271) can be expressed by $G1 \times (\pi \times d13^4/32)$, when the torsional rigidity of the small diameter distal connection portion (281) is defined as k22, the cross sectional second polar moment is defined as Ip22, the transverse elastic modulus is defined as G2 same as the second core-large diameter portion (21B), and the outer diameter of the contact end to the tubular connector (71) is defined as d23, the cross sectional second polar moment Ip22 can be expressed by $(\pi \times d23^4/32)$ and the torsional rigidity k22 of the small diameter distal connection portion (281) can be expressed by $G2 \times (\pi \times d23^4/32)$, when the torsional rigidity of the tubular connector (71) is defined as J1, the transverse elastic modulus is defined as G3, the cross sectional second polar moment is defined as Ip3, the outer diameter is defined as do and the inner diameter is defined as do1, the cross sectional second polar moment Ip3 can be expressed by $[\pi \times (do^4 - do1^4)/32]$ and the torsional rigidity J1 of the tubular connector (71) can be expressed by $G3 \times [\pi \times (do^4 - do1^4)/32]$, and the relational expression (k22/k11)>(J1/k11)>1 between the torsional rigidity ratio (J1/k11) of the torsional rigidity J1 of the tubular connector (71) with respect to the torsional rigidity k11 of the small diameter proximal connection portion (271) and the torsional rigidity ratio (k22/k11) of the torsional rigidity k22 of the small diameter distal connection portion (281) with respect to the torsional rigidity k11 of the small diameter proximal connection portion (271) satisfies the following relational expression from the above described relational expressions (12) (13).

$$[G2 \times d23^4/(G1 \times d13^4)] > [G3 \times (do^4 - do1^4/(G1 \times d13^4)] > 1$$

Preferably, the following relational expression is satisfied.

$$5.00 \geq [G2 \times d23^4/G1 \times d13^4)] > [G3 \times (do^4 - do1^4)/(G1 \times d13^4)] > 1$$

More preferably, the following relational expressions are satisfied.

$$4.85 \geq [G2 \times d23^4/(G1 \times d13^4)] > [G3 \times (do^4 - do1^4)/(G1 \times d13^4)] > 1 \text{ and}$$

$$3.40 \geq [G3 \times (do^4 - do1^4)/(G1 \times d13^4)].$$

Further more preferably, the following relational expression is satisfied.

$$4.50 \geq [G2 \times d23^4/(G1 \times d13^4)] > [G3 \times (do^4 - do1^4)/(G1 \times d13^4)] \text{ and}$$

$$3.20 \geq [G3 \times (do^4 - do1^4)/(G1 \times d13^4)] \geq 1.20.$$

A manufacturing method of the guide wire having the connection structure is as follows.

A manufacturing method of a medical guide wire, the medical guide wire comprising: a first core (2A) having a pseudoelastic property; a second core (2B) having a strain-induced martensitic transformation phase; and a tubular connector (71), the second core (2B) is formed by: a step of applying a solid solution heat treatment on an austenitic stainless steel wire; a step of repeating a plurality of wire drawing processing until a drawing rate becomes between 70% and 99.6%; and a step of applying a low temperature annealing treatment after the final wire drawing is applied, the method comprising:

a step of inserting a distal end of the second core (2B) into the tubular connector (71) from one side of the tubular connector (71), the second core (2B) being formed to have a metamorphosing rate to a strain-induced martensitic transformation phase of between 20% and 80% by the above described steps;

a step of inserting a proximal end of the first core (2A) into the tubular connector (71) from the other side of the tubular connector (71); and a step of connecting and fixing the tubular connector (71) with the first core (2A) and the second core (2B).

The step of the wire drawing of the second core (2B) can be replaced by a step of repeating a plurality of wire drawing processing until the drawing rate becomes between 70% and 85%, or a step of repeating a plurality of wire drawing processing until the drawing rate becomes between 85% and 96%.

The step of applying the solid solution heat treatment on the second core (2B) can be replaced by a step of applying the solid solution heat treatment on the austenitic stainless steel wire (e.g., SUS304, SUS316) in which the chemical abundance is specified to be the lower limit value of the standard value as described above.

Because of this, as described above, the medical guide wire having the connecting structure provided with the second core (2B) capable of remarkably improving the transverse elastic modulus.

Note that, this invention is not limited to the above-mentioned embodiments. Although it is to those skilled in the art, the following are disclosed as the one embodiment of this invention.

Mutually substitutable members, configurations, etc. disclosed in the embodiment can be used with their combination altered appropriately.

Although not disclosed in the embodiment, members, configurations, etc. that belong to the known technology and can be substituted with the members, the configurations, etc. disclosed in the embodiment can be appropriately substituted or are used by altering their combination.

Although not disclosed in the embodiment, members, configurations, etc. that those skilled in the art can consider as substitutions of the members, the configurations, etc. disclosed in the embodiment are substituted with the above mentioned appropriately or are used by altering its combination.

While the invention has been particularly shown and described with respect to preferred embodiments thereof, it should be understood by those skilled in the art that the foregoing and other changes in form and detail may be made therein without departing from the sprit and scope of the invention as defined in the appended claims.

What is claimed is:

1. A medical guide wire comprising:
a first core;
a second core; and
a tubular connector, wherein
the first core has a pseudoelastic property and includes a small diameter proximal connection portion and a first core-large diameter proximal portion in order from the proximal end to the distal end,
the tubular connector has a pseudoelastic property,
the first core-large diameter proximal portion and the tubular connector are a Ni—Ti alloy having the transverse elastic modulus of between 17650 Mpa and 21575 Mpa when an austenite phase is exhibited,
the second core has a strain-induced martensitic transformation phase and includes a second core-large diameter portion and a small diameter distal connection portion in order from the proximal end to the distal end,
the second core-large diameter portion is an austenitic stainless steel wire having the transverse elastic modulus of 68500 Mpa or more,
the small diameter proximal connection portion has a first small diameter proximal portion and a second small diameter proximal portion in order from the distal end to the proximal end,
the outer diameter of the second small diameter proximal portion is gradually reduced from the outer diameter of the first small diameter proximal portion,
the small diameter distal connection portion has a first small diameter distal portion and a second small diameter distal portion in order from the proximal end to the distal end,
the outer diameter of the second small diameter distal portion is gradually reduced from the outer diameter of the first small diameter distal portion, the small diameter proximal connection portion is arranged inside the tubular connector at the distal end of the tubular connector and the small diameter distal connection portion is arranged inside the tubular connector at the proximal end of the tubular connector, the distal end of the tubular connector is in contact with a first step between the first core-large diameter proximal portion and the small diameter proximal connection portion, the first core-large diameter proximal portion having a larger outer diameter than the small diameter proximal connection portion, the proximal end of the tubular connector is in contact with a second step between the second core-large diameter portion and the small diameter distal connection portion, the second core-large diameter portion having a larger outer diameter than the small diameter distal connection portion, and when the torsional rigidity of the first core-large diameter proximal portion is defined as K1, the transverse elastic modulus of the first core-large diameter proximal portion is defined as G1, the outer diameter of a first contact position between the tubular connector and the first core-large diameter proximal portion is defined as D1, the torsional rigidity of the second core-large diameter portion is defined as K2, the transverse elastic modulus of the second core-large diameter portion is defined as G2, the outer diameter of a second contact position between the tubular connector and the second core-large diameter portion is defined as D2, the torsional rigidity of the tubular connector is defined as J1, the transverse elastic modulus of the tubular connector is defined as G3, the outer diameter of the tubular connector is defined as do, and the inner diameter of the tubular connector is defined as do1, the torsional rigidity ratio (K2/K1) of the torsional rigidity K2 of the second core-large diameter portion with respect to the torsional rigidity K1 of the first core-large diameter proximal portion satisfies the following relational expression:

$$K2/K1 = G2 \times D2^4 / (G1 \times D1^4),$$

the torsional rigidity ratio J1/K1 of the torsional rigidity J1 of the tubular connector with respect to the torsional rigidity K1 of the first core-large diameter proximal portion satisfies the following relational expression:

$$J1/K1 = G3 \times (do^4 - do1^4)/(G1 \times D1^4), \text{ and}$$

the torsional rigidity ratio (K2/K1) of the torsional rigidity K2 of the second core-large diameter portion with respect to the torsional rigidity K1 of the first core-large diameter proximal portion satisfies the relational expressions:

$$5.65 \geq (K2/K1) > (J1/K1) > 1; \text{ and}$$

$$4.48 \geq (J1/K1).$$

2. A medical guide wire comprising:
a first core;
a second core; and
a tubular connector, wherein
the first core has a pseudoelastic property and includes a small diameter proximal connection portion and a first core-large diameter proximal portion in order from the proximal end to the distal end,
the tubular connector has a pseudoelastic property,
the small diameter proximal connection portion and the tubular connector are a Ni—Ti alloy having the transverse elastic modulus of between 17650 Mpa and 21575 Mpa when an austenite phase is exhibited, the second core has a strain-induced martensitic transformation phase and includes a second core-large diameter portion and a small diameter distal connection portion in order from the proximal end to the distal end, the small diameter distal connection portion is an austenitic stainless steel wire having the transverse elastic modulus of 68500 Mpa or more, the tubular connector has a constant outer diameter over an entire length, the small diameter proximal connection portion has a first small diameter proximal portion arranged inside the tubular connector at the distal end of the tubular connector, the small diameter distal connection portion has a first small diameter distal portion arranged inside the tubular connector at the proximal end of the tubular connector, the first small diameter proximal portion has a first tapered portion which is in contact with a first inner end portion of the distal end of the tubular connector, the first small diameter distal portion has a second tapered portion which is in contact with a second inner end portion of the proximal end of the tubular connector, when the torsional rigidity of the small diameter proximal connection portion is defined as k11, the transverse elastic modulus of the small diameter proximal connection portion is defined as G1, the outer diameter of a first contact position between the tubular connector and the small diameter proximal connection portion is defined as d13, the torsional rigidity of the small diameter distal connection portion is defined as k22, the transverse elastic modulus of the small diameter distal connection portion is defined as G2, the outer diameter of a second contact position between the tubular connector and the small diameter distal connection portion is defined as d23, the torsional rigidity of the tubular connector is defined as J1, the transverse elastic modulus of the tubular connector is defined as G3, the outer diameter of the tubular connector is defined as do, and the inner diameter of the tubular connector is defined as do1, the torsional rigidity ratio (k22/k11) of the torsional rigidity k22 of the small diameter distal connection portion with respect to the torsional rigidity k11 of the small diameter proximal connection portion satisfies the following relational expression:

$$k22/k11 = G2 \times d23^4/(G1 \times d13^4),$$

the torsional rigidity ratio (J1/k11) of the torsional rigidity J1 of the tubular connector with respect to the torsional rigidity k11 of the small diameter proximal connection portion satisfies the following relational expression:

$$J1/k11 = G3 \times (do^4 - do1^4)/(G1 \times d13^4), \text{ and}$$

the torsional rigidity ratio (J1/k11) of the torsional rigidity J1 of the tubular connector with respect to the torsional rigidity k11 of the small diameter proximal connection portion and the torsional rigidity ratio (k22/k11) of the torsional rigidity k22 of the small diameter distal connection portion with respect to the torsional rigidity k11 of the small diameter proximal connection portion satisfy the following relational expressions:

$$4.85 \geq (k22/k11) > (J1/k11) > 1; \text{ and}$$

$$3.40 \geq (J1/k11).$$

3. The medical guide wire according to claim 2, wherein the torsional rigidity ratio ($J1/k11$) of the torsional rigidity $J1$ of the tubular connector with respect to the torsional rigidity $k11$ of the small diameter proximal connection portion and the torsional rigidity ratio ($k22/k11$) of the torsional rigidity $k22$ of the small diameter distal connection portion with respect to the torsional rigidity $k11$ of the small diameter proximal connection portion satisfy the following relational expressions:

$4.50 \geq (k22/k11) > (J1/k11) > 1$; and $3.20 \geq (J1/k11) \geq 1.20$.

\* \* \* \* \*